(12) United States Patent
Knauf et al.

(10) Patent No.: US 7,344,650 B2
(45) Date of Patent: Mar. 18, 2008

(54) PROCESS FOR THE WORKING-UP OF WASTE WATERS CONTAINING AROMATIC NITRO COMPOUNDS

(75) Inventors: Thomas Knauf, Dormagen (DE); Franz-Ulrich Von Gehlen, Krefeld (DE); Wolfgang Dohmen, Duisburg (DE); Jörg Schmiedler, Duisburg (DE)

(73) Assignee: Bayer MaterialScience AG, Leverkusen (DE)

( * ) Notice: Subject to any disclaimer, the term of this patent is extended or adjusted under 35 U.S.C. 154(b) by 296 days.

(21) Appl. No.: 11/101,261

(22) Filed: Apr. 7, 2005

(65) Prior Publication Data

US 2005/0224424 A1   Oct. 13, 2005

(30) Foreign Application Priority Data

Apr. 10, 2004   (DE) ...................... 10 2004 017 628

(51) Int. Cl.
*C02F 1/02*   (2006.01)
*C02F 101/38*   (2006.01)

(52) U.S. Cl. .................. 210/774; 210/909; 210/919; 568/927

(58) Field of Classification Search ................ 210/909
See application file for complete search history.

(56) References Cited

U.S. PATENT DOCUMENTS

| | | | |
|---|---|---|---|
| 3,844,914 A | 10/1974 | Murchison | 204/158 R |
| 4,230,567 A | 10/1980 | Larbig | 210/600 |
| 4,241,229 A * | 12/1980 | Alexanderson | 568/939 |
| 4,597,875 A * | 7/1986 | Carr et al. | 210/710 |
| 4,925,565 A | 5/1990 | Adams et al. | 210/634 |
| 5,221,440 A | 6/1993 | Miyagi et al. | 203/14 |
| 5,232,605 A | 8/1993 | Baur et al. | 210/761 |
| 5,554,299 A * | 9/1996 | Joulak et al. | 210/712 |
| 6,254,789 B1 * | 7/2001 | Marion et al. | 210/765 |
| 6,288,289 B1 * | 9/2001 | Boyd et al. | 568/934 |
| 6,953,869 B2 * | 10/2005 | Munnig et al. | 568/934 |

FOREIGN PATENT DOCUMENTS

DE   198 15 844 A1   10/1999
EP   1 132 347 A2   9/2001

* cited by examiner

Primary Examiner—Peter A. Hruskoci
(74) Attorney, Agent, or Firm—Lyndanne M. Whalen

(57) ABSTRACT

Alkaline waste waters formed in the washing of crude nitrobenzene which has been prepared by the adiabatic nitration of benzene with nitrating acid, washed in an acidic washing process, and then washed in an alkaline washing process are treated. The alkaline waste water being treated generally contains benzene in a concentration of from about 100 to about 3000 ppm and nitrobenzene in a concentration of from about 1000 to about 10,000 ppm. In the process of the present invention, undissolved benzene and/or nitrobenzene are separated from the alkaline waste water, residual benzene and/or nitrobenzene is/are then optionally stripped out of the alkaline waste water, and the alkaline waste water from which benzene and/or nitrobenzene has been removed is heated to a temperature of from 150 to 500° C. under excess pressure with the exclusion of oxygen.

3 Claims, No Drawings

PROCESS FOR THE WORKING-UP OF WASTE WATERS CONTAINING AROMATIC NITRO COMPOUNDS

BACKGROUND OF THE INVENTION

The present invention relates to a process for the working-up, by thermal pressure decomposition (TPD), of alkaline waste waters formed in the washing of crude nitrobenzene.

In addition to water, the alkaline waste waters from the washing of crude nitrobenzene usually contain residual amounts of benzene and nitrobenzene, as well as nitrohydroxyaromatics. The following nitrohydroxyaromatics, which can also be present in the form of their water-soluble salts, may be mentioned as examples: mono-, di- and trinitrophenols, mono-, di- and trinitrocresols, mono-, di- and trinitroresorcinols and mono-, di- and trixylenols. Possible salt-forming agents are any metals that are capable of forming water-soluble salts with the nitrohydroxyaromatics. The alkali metals, e.g. lithium, sodium, potassium and rubidium, may preferably be mentioned.

The basic TPD process for the treatment of waste waters containing aromatic nitro compounds is described in EP 0 005 203 A2 and EP 0 503 387 A1. EP 0 005 203 A2 describes a process for the working-up of waste waters containing nitrohydroxyaromatics wherein the waste waters are treated at a pressure of 50-250 bar and a temperature of 150-500° C. with the exclusion of air and oxygen.

EP 0 503 387 A1 describes a similar process, but in this case the alkaline waste water is worked up by the addition of nitric acid and subsequent treatment in temperature ranges of 180-350° C. and a pressure range of 40-250 bar.

However, both processes have considerable disadvantages.

EP 0 005 203 A2 does not describe the removal of organic hydrocarbons, such as benzene or nitrobenzene, which are obtained in an adiabatic nitration process corresponding to the state of the art. The purification of the waste water according to the teaching of EP 0 005 203 A2 is therefore inadequate and the consumption of sodium hydroxide solution in the TPD becomes very high.

In EP 0 503 387 A1, the decomposition of nitrobenzene is not complete, so a further treatment of the waste water is necessary. Moreover, the nitrobenzene contained in the waste water is decomposed in the TPD, thereby reducing the yield achieved. The presence of nitric acid in the TPD, which is required according to the teaching of EP 0 503 387 A1, also increases the process costs in several respects: (1) the consumption of nitric acid and (2) the high material burden and the associated high investment costs for a titanium-lined tubular reactor. An additional disadvantage, not mentioned in EP 0 503 387 is the need to neutralize the described alkaline waste water prior to addition of the nitric acid, which can optionally be effected with the appropriate equivalent amount of nitric acid.

SUMMARY OF THE INVENTION

It is an object of the present invention to provide a simple and economic process for the working-up of alkaline waste waters formed in the washing of crude nitrobenzene prepared by the adiabatic nitration of benzene. It is also an object of the present invention to provide a process which requires low investment costs (i.e., does not require titanium-lined apparatuses in the TPD), has a low consumption of NaOH and at the same time has a high purification efficiency.

These and other objects which will be apparent to those skilled in the art are accomplished by separating benzene and/or nitrobenzene from the alkaline waste water and then heating the waste water under pressure to a temperature of from 150 to 500° C. in the absence of oxygen.

DETAILED DESCRIPTION OF THE INVENTION

The invention relates to a process for working-up alkaline waste waters generated from the washing of crude nitrobenzene. The crude nitrobenzene being washed is that which has been prepared by the adiabatic nitration of benzene with nitrating acid. This crude nitrobenzene is first washed in an acidic washing process and then washed in an alkaline washing process. From this alkaline washing process, an alkaline waste water which typically contains benzene in concentrations of from about 100 to about 3000 ppm and nitrobenzene in concentrations of from about 1000 to about 10,000 ppm is generated. It is this alkaline waste water which is treated in accordance with the process of the present invention.

In the process of the present invention, undissolved benzene and/or nitrobenzene are separated from the alkaline waste water. Residual benzene and/or nitrobenzene are then optionally stripped from the alkaline waste water, and the alkaline waste water from which benzene/nitrobenzene has been removed is then heated to a temperature of from 150° to 500° C. under excess pressure with the exclusion of oxygen.

The nitration of benzene to nitrobenzene is conventionally carried out by processes known to those skilled in the art, e.g. according to EP 0 436 443 A2.

The crude nitrobenzene is then washed in an acidic washing process. The concentration of the acid used in this washing process is preferably adjusted to 0.5 to 2 wt. % of sulfuric acid, based on the weight of the aqueous phase.

The crude nitrobenzene is then washed in an alkaline washing process. The pH of alkaline wash is preferably adjusted to a value of $\geq 9$, most preferably, to a pH of from 10 to 14. The alkaline waste water generated from this alkaline washing process typically contains benzene in concentrations of from about 100 to about 3000 ppm, preferably from about 100 to about 1000 ppm, and nitrobenzene in a concentration of from about 1000 to about 10,000 ppm, preferably from about 1200 to about 8,000 ppm. The waste water usually also contains nitrohydroxyaromatics in a concentration of from about 2,000 to about 25,000 ppm. It is the alkaline waste water generated from this alkaline wash which is then worked up by the process of the present invention.

Undissolved benzene and/or nitrobenzene still present in the alkaline waste water are separated from the waste water. The benzene and/or nitrobenzene which have been separated are then preferably recycled into the nitration process or into the crude nitrobenzene. The undissolved nitrobenzene may be separated off by means of separators, settling tanks or any of the other known phase separation apparatuses. It is preferable to use a settling tank. The alkaline waste water remaining after this separation of undissolved benzene and/or nitrobenzene preferably contains benzene in a concentration of from about 100 to about 1,000 ppm and nitrobenzene in a concentration of from about 1,200 to about 3,000 ppm.

Benzene and any residual nitrobenzene can then optionally be stripped out of the alkaline waste water. This is preferably done in a stripping column in which the residual amounts of benzene and nitrobenzene are stripped off at the top by steam distillation. The vapors obtained, containing benzene and nitrobenzene, are then preferably recycled into the alkaline washing process. The stripping column can be monitored for malfunctions, e.g., by means of redundant safety devices. The alkaline waste water remaining after such stripping preferably contains benzene in a concentration of only up to 10 ppm and nitrobenzene in a concentration of up to 10 ppm.

The alkaline waste water from which benzene and/or nitrobenzene have been separated, still contains organic salts of the nitrohydroxyaromatics. It is this waste water which is heated to a temperature of from about 150° to about 500° C., preferably from about 250° to about 350° C., most preferably, from about 270° to about 290° C. under excess pressure with the exclusion of oxygen. It is also possible to heat the waste water under an inert gas atmosphere or under an inert gas admission pressure of, e.g., from 0.1 to 100 bar. Examples of suitable inert gases are nitrogen and/or argon. Depending on the temperature and, if appropriate, the inert gas admission pressure, the absolute-pressures produced when the waste waters are heated preferably range from about 50 to about 350 bar, more preferably, from about 50 to about 200 bar, most preferably from about 70 to about 130 bar. Heating of the alkaline waste water and the thermal decomposition under pressure of the organic constituents present therein are generally carried out for a period of from about 5 to about 120 minutes, preferably, from about 15 to about 30 minutes.

The TPD plant sections can be made of any sufficiently durable material, e.g., steel 1.4571. The sections that make contact with the waste water do not need to be coated with titanium. The waste water treated in accordance with the present invention is preferably passed through a safety device, in which the phenolate content is checked, and can then be discharged, e.g., into a biological sewage treatment plant.

If the optional stripping of benzene and/or nitrobenzene is carried out, benzene and nitrobenzene can be degraded to contents of $\leq 2$ ppm by the process of the present invention. If this stripping process is omitted, nitrobenzene contents of preferably $\leq 400$ ppm, more preferably, $\leq 200$ ppm and benzene contents of preferably $\leq 10$ ppm, more preferably, $\leq 1$ ppm. can be obtained at the outlet of the TPD. The process of the present invention also makes it possible to reduce the nitrohydroxyaromatic content of the TPD to contents of <10 ppm, preferably <5 ppm.

In a preferred embodiment of the process of the present invention, the concentration of aromatics in the alkaline waste water is checked in a safety device after separation of the benzene and/or nitrobenzene and before heating under pressure in order to eliminate a possible explosion hazard in the TPD. This is preferably done by monitoring the phase interface (monitoring that the aqueous phase drawn off is essentially free of organic parts) in the alkaline washing process, monitoring the phase interface in the separation of benzene and nitrobenzene, and monitoring the pH and/or density and optionally also monitoring with an FID (flame ionization detector) after the waste water has been heated under pressure.

Waste waters containing aniline and aminohydroxyaromatics, obtained, e.g., in the preparation of aniline, can also be mixed with the alkaline waste waters from the washing of the crude nitrobenzene. These waste waters from aniline preparation preferably contain aliphatic and aromatic hydrocarbons in concentrations of 1 to 10 ppm and phenols and phenolic salts in concentrations of from about 200 to about 1500 ppm.

The process according to the invention is advantageous in that the removal of substantial amounts of benzene and/or nitrobenzene results in decreased consumption of NaOH during the heating under pressure step. Accordingly, the consumption of NaOH in the process, and the loss of benzene and nitrobenzene due to decomposition in the TPD, are minimized. An immediate advantage of using less NaOH is that it is not necessary to use highly corrosion-resistant materials to construct the plant sections of the TPD. Because overall fewer organic constituents have to be degraded in the TPD due to the prior separation of benzene and nitrobenzene, the capacity of the TPD is ultimately increased and the purity of the waste water worked up in this way is improved. The waste waters treated by the process according to the invention can therefore be discharged directly into a biological sewage treatment plant without dilution.

Having thus described the invention, the following examples are given as being illustrative thereof.

EXAMPLES

Example 1

Comparative Example from EP 0 005 203 A2

1200 ml of an aqueous-alkaline waste water from an adiabatic nitration process were introduced into a nitrogen-flushed 2 liter autoclave equipped with stirrer, manometer and thermometer. Nitrogen was then applied under a pressure of 30 bar. The waste water was then heated to 300° C. and kept at the reaction temperature of 300° C. for 15 minutes (TPD). The pressure rose to 114 bar. After cooling, the waste water was withdrawn and analyzed. Table 1 lists the analytical values for the contents of the various organic substances before and after the thermal pressure decomposition (TPD).

TABLE 1

| Content | before TPD | after TPD |
|---|---|---|
| Na salts of mono-, di- and trinitrophenols | 3100 ppm | 2.6 ppm |
| Sodium hydroxide | 0.25 wt. % | 0.12 wt. % |
| Sodium sulfate | 0.5 wt. % | 0.5 wt. % |
| Sodium nitrate | 1.8 wt. % | 2.1 wt. % |
| Sodium nitrite | 0.04 wt. % | 0.05 wt. % |
| Sodium carbonate | 0.05 wt. % | 0.2 wt. % |

Example 2

Comparative Example from EP 0 503 387 A1

A waste water with the composition indicated in Table 2 was treated in a tubular reactor under the following reaction conditions:

Reaction temperature: 280° to 290° C.

Pressure: 95 bar

Amount of nitric acid added: 1.5 wt. %, based on the weight of waste water

Residence time: 5 min

The analyses of this waste water before and after treatment are reported in Table 2.

TABLE 2

| Analysis of waste water | before treatment | after treatment |
| --- | --- | --- |
| TOC content (TOC: total organic carbon) | 355 mg/l | 17 mg/l |
| Nitrobenzene | 2000 mg/l | 6 mg/l |
| 2,6-Dinitrophenol | 53 mg/l | <100 ppb |
| 2,4-Dinitrophenol | 485 mg/l | <100 ppb |
| Picric acid | 117 mg/l | <50 ppb |

Example 3

Example According to the Invention

The crude nitrobenzene from the adiabatic nitration of benzene was first washed in an acidic washing process and then washed under alkaline conditions in a stirred tank with the addition of sodium hydroxide solution (50%). The mixture was then separated in a first downstream separating tank into an organic phase (crude nitrobenzene) and an aqueous phase (alkaline waste water, waste liquor) on the basis of their density difference. The alkaline waste water was saturated with nitrobenzene and had the composition given in Table 3. It was then passed into another separating tank, where undissolved nitrobenzene and benzene settled out on the bottom and were separated off by phase separation. The alkaline waste water from this separating tank was mixed with waste water from the working-up of aniline and subjected to further treatment by thermal pressure decomposition. Table 3 shows the analytical data for the composition of the alkaline waste water before the first separating tank, after the first separating tank (and after mixing with the waste waters from the working-up of aniline) and after the TPD.

TABLE 3

| Content | before first separating tank | after first separating tank | after TPD |
| --- | --- | --- | --- |
| Nitrobenzene | 4846 ppm | 2538 ppm | 182 ppm |
| Benzene | 357 ppm | 183 ppm | 1 ppm |
| Nitrophenates | 13,568 ppm | 13,508 ppm | <5 ppm |
| NaOH | 1.7 wt. % | 1.7 wt. % | 0.9 wt. % |
| pH | 13.7 | 13.4 | 10.4 |
| Aminophenates | 0 | 1241 ppm | <5 ppm |

The TPD was operated at 100 bar and 290° C. with a residence time of 30 minutes and a narrow residence time distribution.

Example 4

Example According to the Invention

The crude nitrobenzene from the adiabatic nitration of benzene was first washed in an acidic washing process and then washed under alkaline conditions in a stirred tank with the addition of sodium hydroxide solution (32%). The mixture was then separated in a first downstream separating tank into an organic phase (crude nitrobenzene) and an aqueous phase (alkaline waste water, waste liquor) on the basis of their density difference. The alkaline waste water was saturated with nitrobenzene and had the composition given in Table 4. It was then passed into another settling tank, where undissolved nitrobenzene and benzene settled out at the bottom and were separated off by phase separation. The waste liquor was then fed into a stripping column operating with live steam, where nitrobenzene and benzene were stripped off overhead. The alkaline waste water from the bottom of the column had the composition given in Table 4 and was subjected to further working-up by thermal pressure decomposition, a partial stream being analytically monitored by means of FID for the presence of nitrobenzene and benzene.

TABLE 4

| Content | before first separating tank | after first separating tank | after stripping column | after TPD |
| --- | --- | --- | --- | --- |
| Nitrobenzene | 6520 ppm | 1830 ppm | <2 ppm | <1 ppm |
| Benzene | 435 ppm | 155 ppm | <1 ppm | non-detectable |
| Nitrophenates | 12,250 ppm | 12,150 ppm | 11,850 ppm | <5 ppm |
| NaOH | 1.0 wt. % | 1.0 wt. % | 0.9 wt. % | 0.6 wt. % |
| pH | 13 | 13 | 13 | 9.8 |

The TPD was operated at 110 bar and 275° C. with a residence time of 30 minutes and a narrow residence time distribution. After the TPD the waste water had the composition listed in Table 4 and could be discharged directly into a biological sewage treatment plant.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for treating alkaline waste waters containing from tout 100 to about 3000 ppm ben zone and from about 1000 to 10,000 ppm nitrobenzene which waste water was generated by washing crude nitrobenzene produced by adiabatic nitration of benzene with nitric acid with an acid and then an alkaline material comprising:
   a) separating the alkaline waste water into an organic phase containing undissolved benzene and/or nitrobenzene and an aqueous phase of alkaline waste water,
   b) stripping residual benzene and/or nitrobenzene from the aqueous phase of alkaline waste water, and
   c) heating the stripped aqueous phase of alkaline waste water to a temperature of from about 150 to about 500° C. at an absolute pressure of from 50 to 350 bar in the absence of oxygen.

2. The process of claim 1 in which residual benzene and/or nitrobenzene is stripped from the aqueous phase of alkaline waste water in step b) with steam.

3. The process of claim 1 in which the stripped aqueous phase of alkaline waste water is combined with waste waters containing aniline and/or aminohydroxyaromatics prior to step c).

* * * * *